US008623380B2

(12) United States Patent
Florent et al.

(10) Patent No.: US 8,623,380 B2
(45) Date of Patent: Jan. 7, 2014

(54) ACELLULAR PERTUSSIS VACCINE WITH DIPHTHRIAE- AND TETANUS-TOXOIDS

(75) Inventors: Patrick Florent, Brussels (BE); Jean Stephenne, Rixensart (BE); Christian Vandecasserie, Lasne (BE)

(73) Assignee: GlaxoSmithKline Biologicals S.A., Rixensart (BE)

( * ) Notice: Subject to any disclaimer, the term of this patent is extended or adjusted under 35 U.S.C. 154(b) by 71 days.

(21) Appl. No.: 10/838,577

(22) Filed: May 4, 2004

(65) Prior Publication Data

US 2004/0208898 A1    Oct. 21, 2004

Related U.S. Application Data

(63) Continuation of application No. 09/827,785, filed on Apr. 6, 2001, now abandoned, which is a continuation of application No. 09/284,887, filed as application No. PCT/EP97/06180 on Nov. 4, 1997, now abandoned.

(30) Foreign Application Priority Data

Nov. 7, 1996   (GB) .................................. 9623233.5

(51) Int. Cl.
| | |
|---|---|
| *A61K 39/10* | (2006.01) |
| *A61K 39/02* | (2006.01) |
| *A61K 39/116* | (2006.01) |
| *A61K 39/05* | (2006.01) |
| *A61K 39/00* | (2006.01) |
| *A61K 38/00* | (2006.01) |

(52) U.S. Cl.
USPC .................. 424/203.1; 424/184.1; 424/234.1; 424/236.1; 424/240.1; 424/238.1; 424/245.1; 514/1.1

(58) Field of Classification Search
USPC .......... 424/184.1, 189.1, 201.1, 202.1, 203.1, 424/204.1, 226.1, 227.1, 234.1, 236.1, 424/239.1, 240.1, 253.1, 254.1, 256.1, 450; 530/350, 112
See application file for complete search history.

(56) References Cited

U.S. PATENT DOCUMENTS

| | | | |
|---|---|---|---|
| 4,695,454 A | 9/1987 | Prince et al. ................ | 424/227.1 |
| 5,429,818 A | 7/1995 | Inzana ......................... | 424/256.1 |
| 5,895,655 A | 4/1999 | Eckhardt et al. ........... | 424/238.1 |
| 5,972,346 A | 10/1999 | Hauser et al. | |
| 6,013,264 A | 1/2000 | Petre et al. .................. | 424/227.1 |
| 6,696,065 B1 * | 2/2004 | Fahim et al. ................ | 424/254.1 |

FOREIGN PATENT DOCUMENTS

WO    WO 93/24148    9/1993

OTHER PUBLICATIONS

Feery, et al., Diphtheria Immunization in Adolescents and Adults with Reduced Doses of Adsorbed Diphtheria Toxoid. *Med. J. Australia*, 1: 128-130 (1981).
Edwards, et al., "Comparison of 13 Acellular Pertussis Vaccines: Overview and Serologic Response". *Pediatrics*, 96 (3 Part 2): 548-557 (1995).
Podda, et al., "Comparative Study of a Whole-Cell Pertussis Vaccine and a Recombinant Acellular Pertussis Vaccine". *Journal of Pediatrics*, 124(6): 921-926 (1994).
Greco, et al., "A Controlled Trial of Two Acellular Vaccines and One Whole-Cell Vaccine Against Pertussis. Progetto Pertosse Working Group". *New England Journal of Medicine*, 334(6): 341-348 (1996).
Englund, et al., "Acellular and Whole-Cell Pertussis Vaccines as Booster Doses: A Multicenter Study". *Pediatrics*, 93(1): 37-43 (1994).
Rennels, et al., "Extensive Swelling After Booster Doses of Acellular Pertussis-Tetanus-Diphtheria Vaccines". *Pediatrics*, 105(1): 1-6 (2000).
Campins-Marti, et al., "Recommendations are Needed for Adolescent and Adult Pertussis Immunisation: Rationale and Strategies for Consideration". *Vaccine*, 20: 641-646 (2002).
U.S. Department of Health and Human Services. "Diphtheria, Tetanus and Pertussis Vaccines. What you Need to Know." *Vaccine Information Sheet*. (2001).
Van der Wielen, et al., "A Randomised Controlled Trial with a Diphtheria-Tetanus-Acellular Pertussis (dTpa) Vaccine in Adults". *Vaccine*, 18: 2075-2082 (2000).
Halperin, et al., "Adverse Reactions and Antibody Response to Four Doses of Acellular or Whole Cell Pertussis Vaccine Combined with Diphtheria and Tetanus Toxoids in the First 19 Months of Life". *Vaccine*, 14(8): 767-772 (1996).
Pichichero, et al., "Antibody Response and Reactions to Completion of a Four-Dose Series with a Two- or Three-Component Acellular Pertussis Vaccine Compared to Whole Cell Pertussis Vaccine". *Scand. J. Infect. Dis.*, 28: 159-163 (1996).
Halperin, et al., "Acellular Pertussis Vaccine as a Booster Dose for Seventeen- to Nineteen-Month-Old Children Immunized with Either Whole Cell or Acellular Pertussis Vaccine at Two, Four and Six Months of Age". *Pediatr. Infect. Dis. J.*, 14: 792-797 (1995).
Edwards, et al., *JAMA*, 269(1): 53-56 (1993).
Englund et al., *J. Infect. Dis.*, 166(6): 1436-1441 (1992).
Hewlett. *Tokai J. exp. Clin Med.*, 13(Suppl): 125-128 (1988).
Keitel et al. *Seminars in Resp. Infect.*,'10(1): 51-57 (1995).
Shefer et al., *J. Infect. Dis.*, 171(4): 1053-1056 (1995).
CDC: Recommended Childhood Immunization Schedule, United States, Jan.-Dec. 1998.

(Continued)

*Primary Examiner* — S. Devi
(74) *Attorney, Agent, or Firm* — Alice P. Bradney

(57) ABSTRACT

The invention provides a diphtheria, tetanus and pertussis vaccine comprising a low dose of each of diphtheria toxoid (D), tetanus toxoid (T), pertussis toxin (PT), filamentous haemagglutinin (FHA) and pertactin (69K). The vaccine maintains an ability to prevent pertussis while showing exceptionally low reactogenicity. Combination vaccines comprising additional antigens are also provided.

3 Claims, 10 Drawing Sheets

(56) References Cited

OTHER PUBLICATIONS

Keitel et al., "Dose-Response Comparisons of 5 Acellular Pertussis Vaccines in Healthy Adults". *Abstract of IDSA, #286, 34th Annual Meeting* (May 1996).
Cardoz et al. Workshop on Acellular Pertussis Vaccines: Transcript of a Workshop Sponsored by the Interagency Group to Monitor Vaccine Development, Production, and Usage, pp. 131-134 (1986).
Granstrom et al. Eur. J. of Clin. Microbiol., 6(1): 18-21 (1987).
Rutter et al. Vaccine, 6: 29-32 (1988).
Sekura et al. The Journal of Pediatrics, 113(5): 806-813 (1988).
Reynolds, E. et al., Vaccine 24: 3248-3257 (2006).
Southern J. et al., Vaccine 23: 3829-3835 (2005).
Zepp, F. et al., Vaccine 25: 5248-5252 (2007).
Meyer, C.U. et al., Clin. Vaccine Immunol. 14: 288-292 (2007).
Minh, et al. "Acellular Vaccines Containing Reduced Quantities of Pertussis Antigens as a Booster in Adolescents". *Pediatrics*, 104(6): 1-6 (1999). http://www.pediatrics.org/cgi/content/full/104/6/e70.
Minh, et al. "Antibody and Cell-Mediated Immune Responses to Booster Immunization with a New Acellular Pertussis Vaccine in School Children". *Vaccine*, 16(17): 1604-1610 (1998).
Sesardic, et al. "Non-Pertussis Components of Combination Vaccines: Problems with Potency Testing". *Biologicals*, 27: 177-181 (1999).

\* cited by examiner

Fig. 1 Anti-PT Results

Fig. 2 Anti-FHA Results

Fig. 3 Anti-PRN Results

| Pain | dtpa | dT |
|---|---|---|
| ≤ 48 h | 58 | 60 |
| 15 days | 60 | 60 |
| Severe | 0 | 0 |
| Redness | | |
| ≤ 48 h | 30 | 37 |
| 15 days | 30 | 37 |
| > 20 MM | 17 | 20 |
| Swelling | | |
| ≤ 48 h | 30 | 37 |
| 15 days | 30 | 37 |
| > 20MM | 5 | 8.3 |
| Fever | | |
| ≤ 48 h | 7 | 7 |
| 15 days | 8 | 8 |
| > 39°C | 0 | 0 |

Fig. 7 % Reporting dtpa 005 - Reactogenicity

| Anti-D | dtpa | dT |
|---|---|---|
| Pre | | |
| ≥ 0.1 | 44% | 44% |
| Post | | |
| ≥ 0.1 | 80% | 78% |
| GMT | 0.85 | 0.81 |
| Anti-T | | |
| Pre | | |
| ≥ 0.1 | 88% | 88% |
| Post | | |
| ≥ 0.1 | 97% | 100% |
| GMT | 7.37 | 13.6 |

Fig. 8 dtpa 005

|  | Pain Week 1 | Moderate Pain Week 1 | Erythema Week 1 | Pain Weeks 2-4 | Erythema Weeks 2-4 |
|---|---|---|---|---|---|
| SB-Med (N=31) | 90 | 10 | 10 | 17 | 3 |
| Placebo (N=31) | 19 | 3 | 3 | 3 | 0 |

- No serious adverse events
- No severe pain
- 2 subjects with hives (days 1-4; days 18-22)

Fig. 9 % Reporting AAPT- Reactogenicity

| Pain | dtpa | dT |
|---|---|---|
| ≤ 48 h | 69 | 70 |
| 15 days | 69 | 70 |
| Severe | 0 | 1 |
| Redness | | |
| ≤ 48 h | 12 | 20 |
| 15 days | 12 | 20 |
| > 30 MM | 1 | 9 |
| Swelling | | |
| ≤ 48 h | 12 | 28 |
| 15 days | 13 | 30 |
| > 30MM | 7 | 15 |
| Fever | | |
| ≤ 48 h | 5 | 6 |
| 15 days | 13 | 15 |
| > 39°C | 0 | 1 |

Fig. 10 % Reporting dtpa 003 - Reactogenicity

| Anti-D | dtpa | dT |
|---|---|---|
| Pre | | |
| ≥ 0.1 | 72% | 72% |
| Post | | |
| ≥ 0.1 | 100% | 100% |
| GMT | 3.3 | 10.5 |
| Anti-T | | |
| Pre | | |
| ≥ 0.1 | 94% | 99% |
| Post | | |
| ≥ 0.1 | 100% | 100% |
| GMT | 22.9 | 54.5 |
Fig. 11 Antibody responses dtpa 003
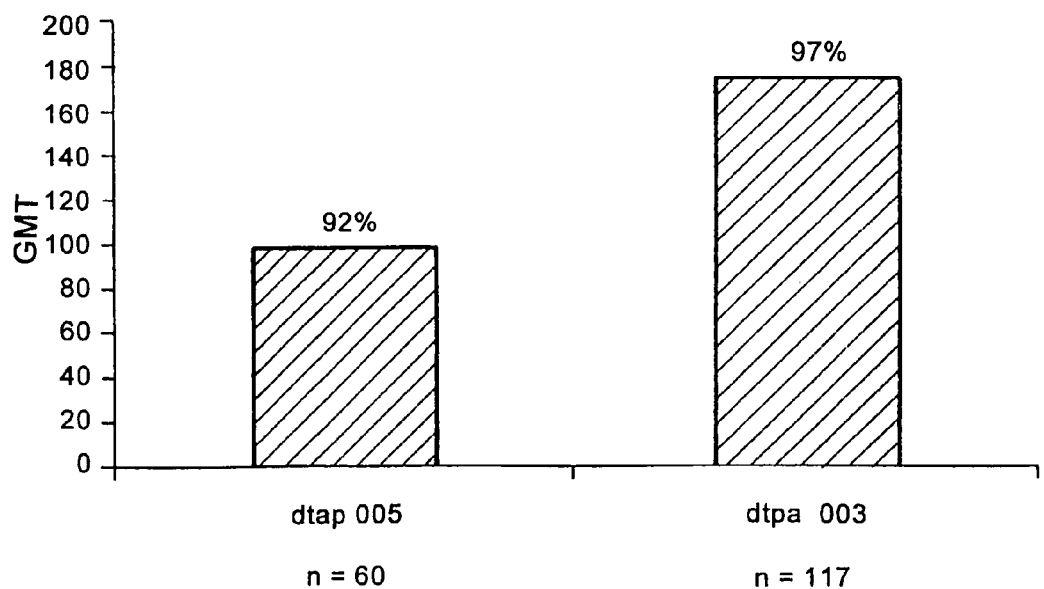
Fig. 12 Anti-PT Results

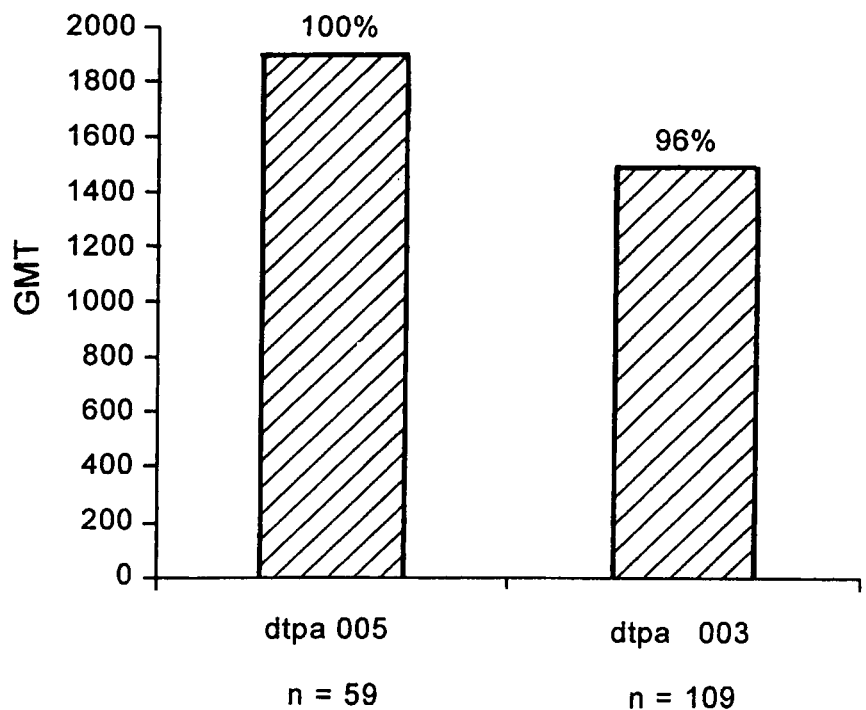
Fig. 13 Anti-FHA Results
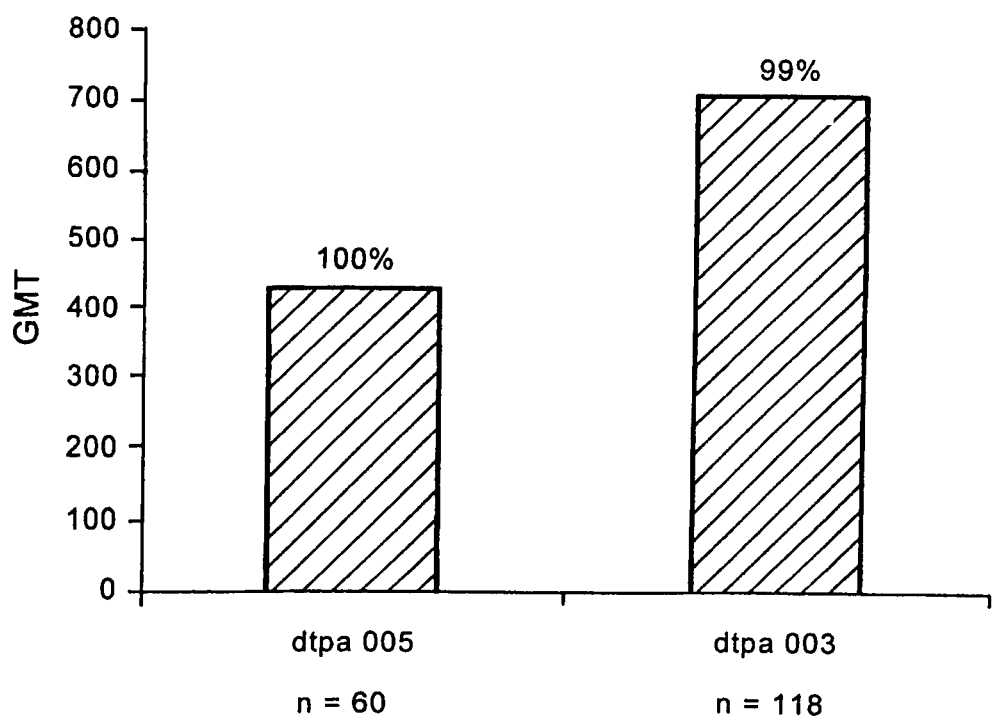
Fig. 14 Anti-PRN Results

ACELLULAR PERTUSSIS VACCINE WITH DIPHTHRIAE- AND TETANUS-TOXOIDS

This application is a continuation of U.S. application Ser. No. 09/827,785, filed Apr. 6, 2001, (now abandoned), which is a continuation of U.S. application Ser. No. 09/284,887, filed May 27, 1999 (now abandoned), which is a 371 US National Stage of International Application No. PCT/EP97/06180, filed Nov. 4, 1997.

The present invention relates to new vaccine formulations, comprising a low dose of the 69 kda outer membrane protein of Bordetella pertussis (hereinafter termed '69K' or '69K antigen' or pertactin, disclosed in European Patent 0 162 639. Recombinant 69K (P69) has been described by N F Fairweather et al, Symposium On Pertussis (Bethesda), 26-28 September 1990). The invention in particular relates to a vaccine comprising more than one antigen, especially a multivalent vaccine, that is: a vaccine for the amelioration or treatment of more than one disease state, in which a low dose of 69K is present. The present invention also relates to the production and use of such vaccines in medicine.

It is known that 69K is an important component of acellular pertussis vaccines (Pa vaccines) for the effective prevention of pertussis.

A study on the dose responses of 5 acellular pertussis vaccines in healthy adults was published by the US National Institutes of Health (NIH) in May 1996 by Keitel, W. et al.

69K -containing vaccines including 'trivalent' vaccines comprising antigens against diphtheria (D), tetanus (T) and pertussis (Pa) have been described in clinical trials conducted in Italy and Sweden and are marketed [for example under the Trade Mark INFANRIX-DTPa (SmithKline Beecham Biologicals)]. Typically the pertussis component of such vaccines comprises pertussis toxin (PT), filamentous haemagglutinin (FHA) and 69K. In INFANRIX-DTPa (Trade Mark) the amounts of D:T:PT:FHA:69K are typically 25 Lf:10 Lf: 25 ug:25 ug:8 ug per 0.5 ml dose of bulk vaccine.

Other multivalent vaccines comprising 69K are also known, for example vaccines comprising an antigen against hepatitis B and antigens against diphtheria, tetanus and pertussis (Hep B, DTPa) were described in WO 93/24148. In such formulations the quantity of D:T:PT:FHA:69K was given as 25 Lf:10 Lf:25 ug:25 ug:8 ug per 0.5 ml dose of bulk vaccine.

It has now been found that a diphtheria, tetanus and pertussis vaccine containing a low dose of each of diphtheria toxoid (D), tetanus toxoid (T), PT, FHA and 69K (herein such a low dose formulation is abbreviated to a dtpa vaccine) maintains an ability to prevent pertussis (and is highly effective in this respect) while having the advantage of showing exceptionally low reactogenicity. Within the limits described herein such vaccines are safe when administered to human subjects and induce rapid protection against infection. In combination vaccines comprising dtpa and other antigens it has been found that there is no interference, i.e. such vaccines show no loss of immunogenicity, and are effective when administered to humans.

In particular the vaccines of this invention are suitable for administration to children as a booster following prior administration of one or more (typically up to about 3) doses of a vaccine comprising a higher dose of D, T, and Pa antigens such as the INFANRIX-DTPa vaccine described above (D:T: PT:FHA:69K=25 Lf:10 Lf:25 ug:25 ug:8 ug per 0.5 ml dose of bulk vaccine). The vaccines of this invention are also of great value for administration to adults and adolescents.

BRIEF DESCRIPTION OF THE DRAWINGS:

FIG. 7 is a table reporting the reactogenicity of the dtpa 005 vaccine, according to the present invention;

FIG. 8 is a table reporting the anti-tetanus and anti-diphtheria titers pre- and post-immunization with the dpta 005 vaccine, according to the present invention;

FIG. 9 is a table reporting the long term side effects of immunization with the dtpa 005 vaccine, according to the present invention;

FIG. 10 is a table reporting the reactogenicity of the dtpa 003 vaccine, according to the present invention;

FIG. 11 is a table reporting the anti-tetanus and anti-diphtheria titers pre- and post-immunization with the dpta 003 vaccine, according to the present invention;

FIG. 12 is a bar graph comparing the anti-PT titers post-immunization with the dpta 005 and dpta 003 vaccines, according to the present invention;

FIG. 13 is a bar graph comparing the anti-FHA titers post-immunization with the dpta 005 and dpta 003 vaccines, according to the present invention; and FIG. 14 is a bar graph comparing the anti-PRN titers post-immunization with the dpta 005 and dpta 003 vaccines, according to the present invention;

Figure 1:
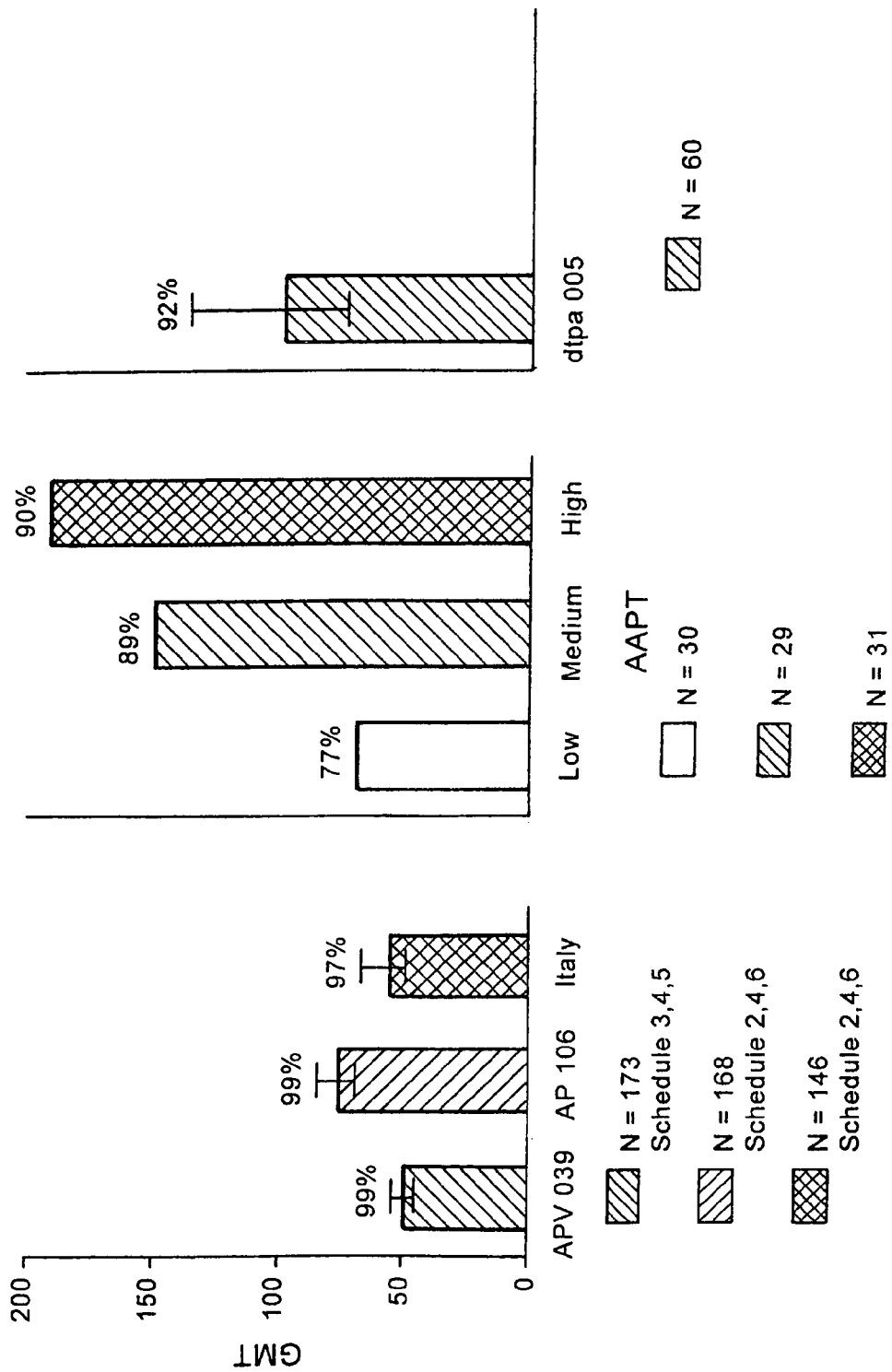
FIG. 1 is a bar graph representing anti-PT titers according to one aspect of the present invention.
Figure 2:
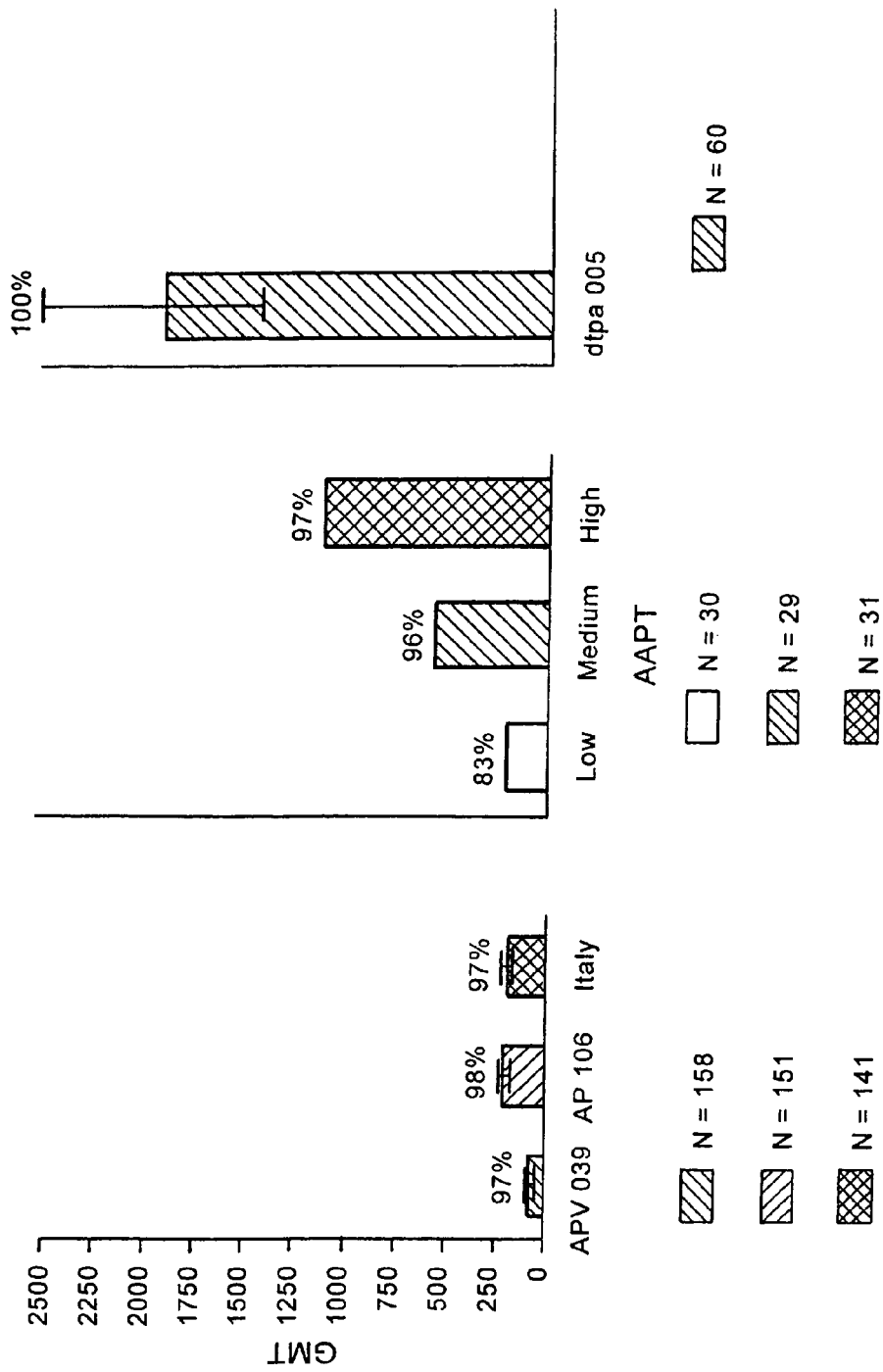
FIG. 2 is a bar graph representing anti-FHA titers according to one aspect of the present invention.
Figure 3:
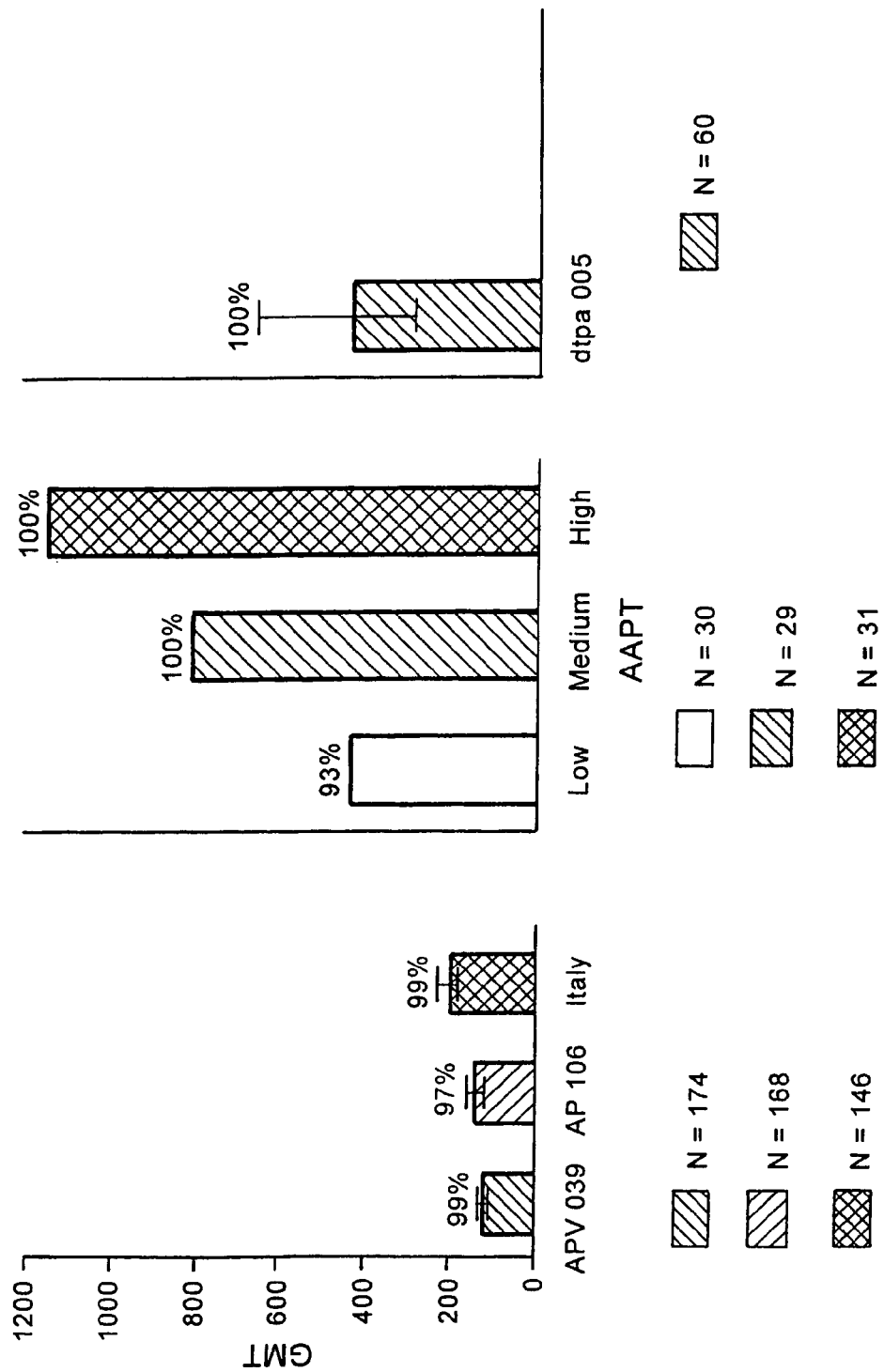
FIG. 3 is a bar graph representing anti-PRN titers according to one aspect of the present invention.
Figure 4:
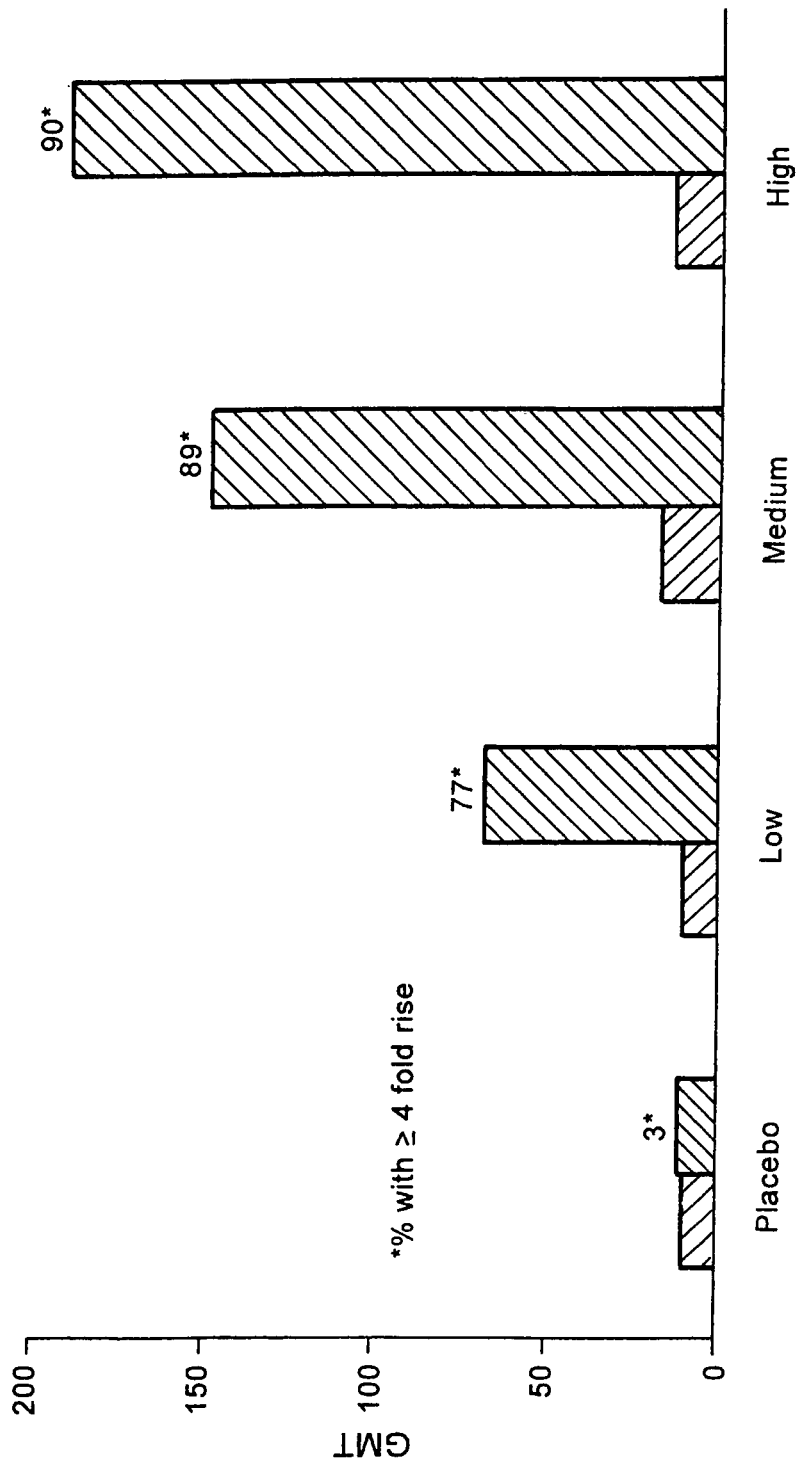
FIG. 4 is a bar graph representing the anti-PT titers for low, medium and high PT vaccine levels, according to the present invention.
Figure 5:
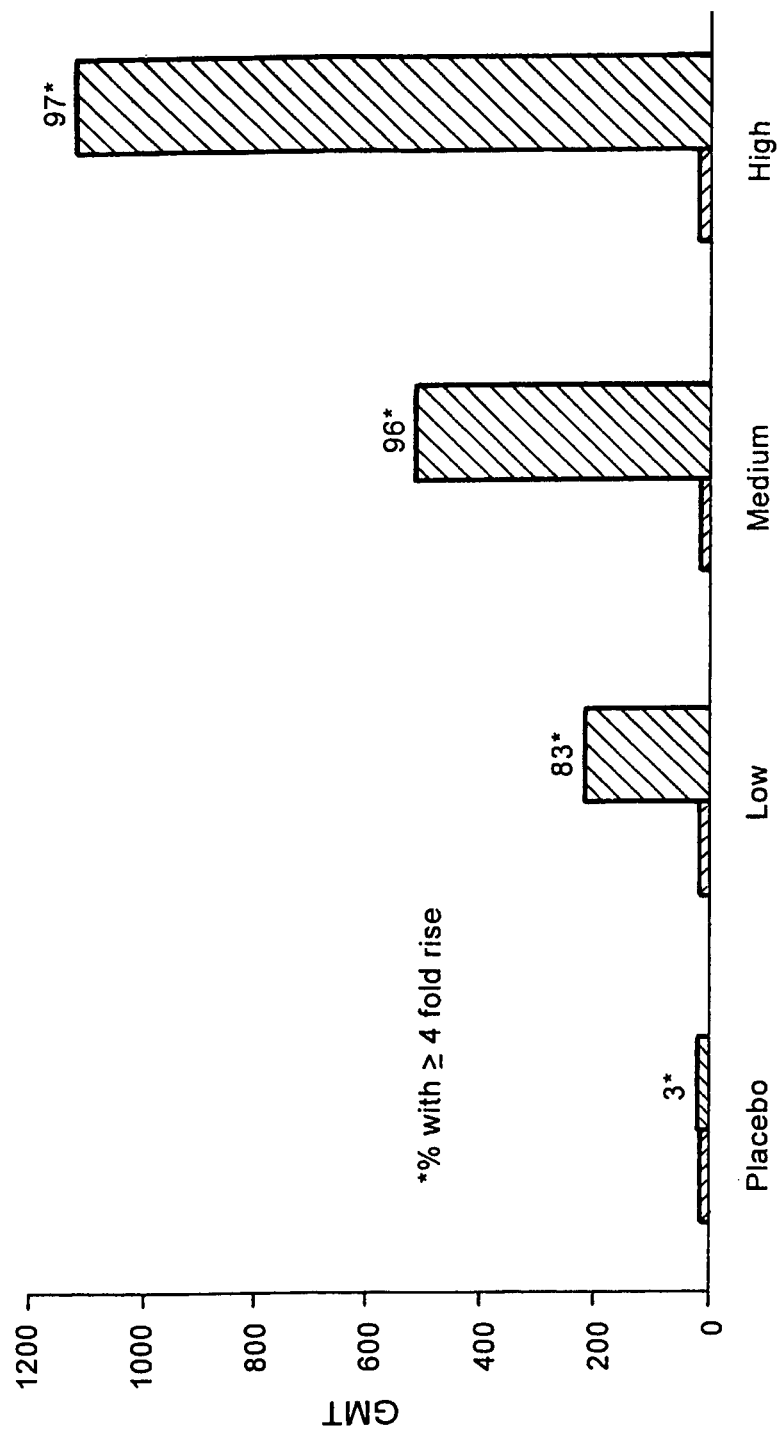
FIG. 5 is a bar graph representing the anti-FHA titers for low, medium and high FHA vaccine levels, according to the present invention.
Figure 6:
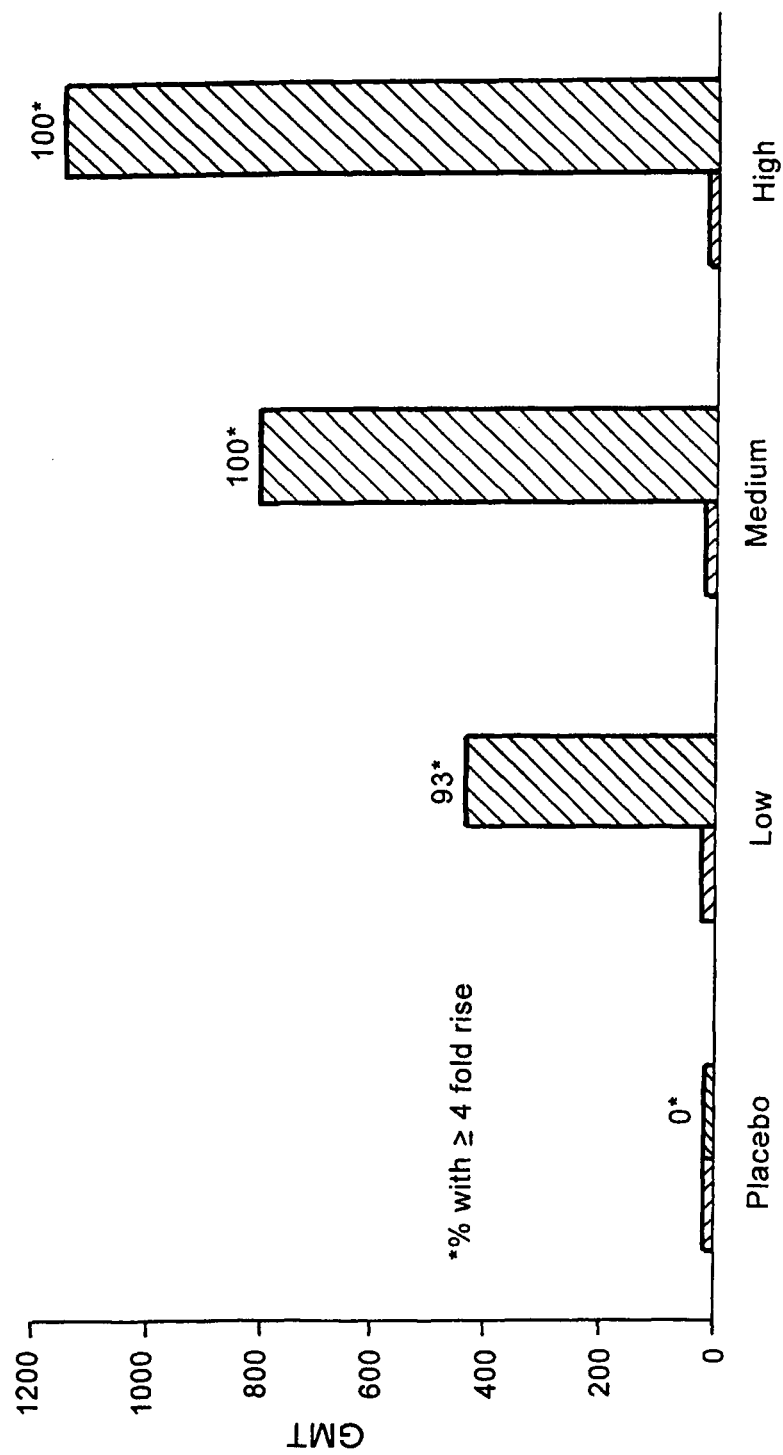
FIG. 6 is a bar graph representing the anti-PRN titers for low, medium and high PRN vaccine levels, according to the present invention.

Accordingly the present invention provides a vaccine composition comprising a low dose of each of the antigens D, T, PT, FHA and 69K (i.e. a dtpa vaccine composition). It will be understood that the vaccine composition of the invention is formulated with a suitable carrier or adjuvant.

By dtpa vaccine or dtpa vaccine composition is meant a dose wherein the concentration of D per 0.5 ml dose of bulk vaccine does not exceed 5 Lf and is preferably 1-4 Lf, more preferably about 2 Lf; the concentration of T per 0.5 ml dose of bulk vaccine does not exceed 10 Lf and is preferably 2.5-7.5 Lf, more preferably about 5 Lf: the concentration of PT per 0.5 ml dose of bulk vaccine does not exceed 10 ug and is preferably 2-10 ug, more preferably about 8 ug; the concentration of FHA per 0.5 ml dose of bulk vaccine does not exceed 10 ug and is preferably 2-10 ug, more preferably about 8 ug; and the concentration of 69K does not exceed 4 micrograms per 0.5 ml dose of bulk vaccine and is preferably in the range 0.5 ug to 3 ug per 0.5 ml dose of bulk vaccine. More preferably the concentration of 69K in the vaccine is in the range 2 to 3 ug, more preferably aproximately 2.5 ug pertactin per 0.5 ml dose of bulk vaccine.

In one aspect the the vaccine compositions of the invention may, for example, comprise (approximately) PT (2.5 ug), FHA (2.5 ug), 69K (0.8 ug) per 0.5 ml dose of bulk vaccine.

In a preferred aspect the vaccine compositions of the invention comprise (approximately) PT (8 ug), FHA (8 ug), 69K (2.5 ug) per 0.5 ml dose of bulk vaccine.

In an especially preferred aspect the vaccine compositions of the invention comprise PT (8 ug), FHA (8 ug), 69K (2.5 ug), D (2 Lf) and T (5 Lf) per 0.5 ml dose of bulk vaccine. This was used in the 'dtpa 005' study reported below.

In another preferred aspect the vaccine composition of the invention has the amount of the D component increased to 2.5 Lf.

In a further preferred aspect the dtpa tricomponent vaccine composition is as follows:
PT 8 μg
FHA 8 μg
69K 2.5 μg
diphtheria toxoid >=2 IU
tetanus toxoid >=20 IU
Al salts 0.3 mg
phenoxyethanol 2.5 mg
This was used in the study in adolescents known as 'dtpa 003', results of which are given below.

Optionally the PT component may be recombinant (for example as described in European Patent Applications EP 0 306 318, EP 0 322 533, EP 0 396 964, EP 0 322 115 and EP 0 275 689) or the PT component may be toxoided, for example as described in EP 0 515 415. See also EP 0 427 462 and WO 91/12020 for the preparation of pertussis antigens.

In a further aspect the invention provides a vaccine composition comprising dtpa (as hereinabove defined) in combination with one or more additional antigens, particularly an antigen against hepatitis B (Hep B) (i.e. a Hep B—dtpa vaccine). Such multivalent vaccines are generally as described in WO 93/24148 except that a low dose of each of D, T, PT, FHA and 69K as hereinabove defined is used in the formulation. As described in WO 93/24148 the hepatitis B antigen is preferably hepatitis B surface antigen.

The dose of hepatitis B surface antigen will normally be in the range 5-20 ug per 0.5 ml dose of bulk vaccine.

The preparation of Hepatitis B surface antigen (HBsAg) is well documented. See for example, Harford et al in *Develop. Biol. Standard* 54, page 125 (1983), Gregg et al in *Biotechnology*, 5, page 479 (1987), EP-A-0 226 846, EP-A-0 299 108 and references therein.

As used herein the expression 'Hepatitis B surface antigen' or 'HBsAg' includes any HBsAg antigen or fragment thereof displaying the antigenicity of HBV surface antigen. It will be understood that in addition to the 226 amino acid sequence of the HBsAg S antigen (see Tiollais et al, Nature, 317, 489 (1985) and references therein) HBsAg as herein described may, if desired, contain all or part of a pre-S sequence as described in the above references and in EP-A-0 278 940. HBsAg as herein described can also refer to variants, for example the 'escape mutant' described in WO 91/14703. In a further aspect the HBsAg may comprise a protein described as L* in European Patent Application Number 0 414 374, that is to say a protein, the amino acid sequence of which consists of parts of the amino acid sequence of the hepatitis B virus large (L) protein (ad or ay subtype), characterised in that the amino acid sequence of the protein consists of either:
  (a) residues 12-52, followed by residues 133-145, followed by residues 175-400 of the said L protein; or
  (b) residue 12, followed by residues 14-52, followed by residues 133-145, followed by residues 175-400 of the said L protein.

HBsAg may also refer to polypeptides described in EP 0 198 474 or EP 0 304 578.

Normally the HBsAg will be in particle form. It may comprise S protein alone or may be as composite particles, for example (L*,S) wherein L* is as defined above and S denotes the S-protein of hepatitis B surface antigen.

Preferably the HBsAg will be adsorbed on aluminium phosphate as described in WO93/24148. Other antigens may be adsorbed onto aluminium phosphate or aluminium hydroxide but in some cases satisfactory results will be obtained only if the other antigen is adsorbed on aluminium phosphate.

Other antigens may included in vaccines of the invention to provide other multivalent vaccines for paediatric, adolescent or adult use. Suitable said other antigens may, for example, comprise those known in the art to provide protection against Haemophilus influenzae b (Hib) and/or polio (IPV) and/or hepatitis A, as described in WO 93/24148.

Suitable components for use in such vaccines are already commercially available and details may be obtained from the World Health Organisation. For example the IPV component may be the Salk inactivated polio vaccine. The component affording protection against Hepatitis A is preferably the product known as 'Havrix' (SmithKline Beecham Biologicals) which is a killed attenuated vaccine derived from the HM-175 strain of HAV [see 'Inactivated Candidate Vaccines for Hepatitis A' by F. E. Andre, A Hepburn and E. D'Hondt, *Prog Med. Virol.* Vol 37, pages 72-95 (1990) and the product monograph 'Havrix' published by SmithKline Beecham Biologicals (1991)]. Conveniently, the Hepatitis B component may comprise the 'S' antigen as already present in the commercial vaccine 'Engerix-B' (SmithKline Beecham Biologicals).

The amount of antigen in each vaccine dose is selected as an amount which induces an immunoprotective response without significant, adverse side effects in typical vaccinees. Such amount will vary depending on which specific immunogens are employed. Generally it is expected that each dose will comprise 15-50 ug of total immunogen. Booster injections may be given. Booster injections of vaccines according to the invention in subjects primed with a vaccine comprising whole cell pertussis (Pw) are as efficacious as in subjects primed with a vaccine comprising acellular pertussis (Pa).

In general the vaccine formulations of any aspect of the invention can be prepared as follows. The required components are adsorbed onto a suitable adjuvant, most especially aluminium hydroxide or aluminium phosphate. After allowing time for complete and stable adsorption of the respective components, the different components can be combined under appropriate conditions.

In a preferred aspect of preparing a combined Hepatitis B-containing vaccine composition according to the invention there is provided a method which involves mixing aluminium phosphate-adsorbed HBsAg with one or more aluminium hydroxide or aluminium phosphate-adsorbed antigens.

The following examples illustrate the invention:

EXAMPLE 1

Preparation of a dtpa Vaccine Formulation and Study in Adults

The dtpa vaccine according to the invention was prepared by standard methodology in accordance with the procedure for formulating a higher dose DTPa vaccine described in WO 93/24148.

Results obtained with the vaccine in a clinical study in adults coded 'dtpa 005' are shown in the appended figures, in which dtpa is used to signify a vaccine according to the invention and PRN is an abbreviation for pertactin (69K ). The abbreviation dT is used to signify the standard diphtheria-tetanus vaccine obtainable from Behringwerke comprising a low dose of diphtheria toxoid and a higher dose of tetanus toxoid.

An open, randomised single dose study was carried out in adults aged 18-45 in Belgium using dtpa formulated as described above in 60 subjects as compared with dT (Behring) in 60 subjects.

For the dtpa group 28 females were studied (mean age 33 years) and 32 males were studied (mean age 33 years). For the dT group 32 females were studed (mean age 34 years) and 28 males were studied (mean age 35 years).

Excluded were those who had had a diphtheria, tetanus or pertussis vaccination within the last 10 years or pertussis disease within the last 5 years.

Sera were obtained pre and I month post vaccination with a solicited follow-up after 15 days and an unsolicited follow-up after 30 days.

Reactogenicity data, antibody responses, anti-PT results, anti-FHA results and anti-PRN (pertactin) results are shown in the appended figures.

In the appended figures, results are also shown for the monovalent pa vaccine used in the NIH (AAPT) studies reported by Keitel et al. References to SmithKline Beecham's (SB's) High, Medium (SB-Med) and Low formulations contain, respectively, PT: (25 ug), FHA (25 ug) and 69K (8 ug) (High); PT (8 ug), FHA (8 ug) and 69K (2.5 ug) (Medium); and PT (2.5 ug), FHA (2.5 ug) and 69K (0.8 ug) (Low).

The abbreviation 'ug' stands for micrograms.

It may be seen that a dtpa vaccine according to the invention was safe and immunogenic in adults. Furthermore immune responses to candidate vaccines of the invention in adults appeared to be at least several times higher than observed for known higher dose DTPa vaccines previously administered to US, German and Italian infants.

EXAMPLE 2

Study in Adolescents ('dtpa 003')

An open, randomised single dose study was carried out in adolescents aged 10-12 in Finland using dtpa formulated as described above in 120 subjects as compared with dT (Finland) in 120 subjects. The same lot of dtpa vaccine of the invention was used in both the dtpa 005 and dtpa 003 studies.

The commercially available (Finland) dT contained: diphtheria toxoid >=4 IU tetanus toxoid >=40 IU For the dtpa group 70 females were studied (mean age 10.9 years) and 49 males were studied (mean age 10.8 years). For the dT group 62 females were studed (mean age 10.9 years) and 56 males were studied (mean age 11.0 years).

The subjects included in the trial had received up to 4 doses of DTPw within the first 2 years of life.

Subjects excluded from the study were those who had had D, T or P vaccination after the second year of life or a history of diphtheria, tetanus or pertussis disease.

Sera were obtained pre and 1 month post vaccination with a solicited follow-up after 15 days and an unsolicited follow-up after 30 days.

Reactogenicity data, antibody responses, anti-PT results, anti-FHA results and anti-PRN (pertactin) results are shown in the appended figures.

It may be seen from the results that a dtpa vaccine according to the invention was safe and immunogenic in adolescents.

Note: In the figures, results relating to the antibody responses for the study in adults (dtpa 005) and the study in adolescents (dtpa 003) show the distribution of individual pre- and post-vaccination anti-diphtheria and anti-tetanus antibody titres of subjects included in the overall analysis of immunogenicity (>=0.1 IU/ml being the cut-off determined for protection). Also given are the geometric mean anti-diphtheria and anti-tetanus antibody titres in IU/ml.

The figures for the dtpa 005 and dtpa 003 studies which illustrate anti-PT, anti-FHA and anti-PRN titers show the vaccine response rate (in % of the total number of subjects-n-) and geometric mean antibody titres (GMT, in EU/ml) for the vaccine components PT, FHA and PRN of subjects included in the overall analysis of immunogenicity.

EXAMPLE 3

Preparation of a Hep B—dtpa Vaccine

The formulation was prepared exactly as in Example 5 of WO93/24148 except that low doses of D, T, PT, FHA and 69K as hereinabove defined were used to make up 0.5 ml dose of bulk vaccine.

In a preferred composition the amounts of dtpa were approximately as follows: PT (8 ug), FHA (8 ug), 69K (2.5 ug), D (2 Lf) and T (5 Lf) per 0.5 ml dose of bulk vaccine.

In another preferred composition the amount of D was increased to 2.5 Lf.

The amount of hepatitis B surface antigen in the vaccine composition can vary from 5-20 ug and is typically 10 ug per 0.5 ml dose of bulk vaccine.

The invention claimed is:

1. A method of boosting immunity against diphtheria, tetanus, and pertussis in an adolescent or adult subject previously vaccinated with a DTPa vaccine, wherein the diphtheria, the tetanus, and the pertussis components of said DTPa vaccine are diphtheria (D) toxoid, tetanus (T) toxoid, pertussis toxoid (PT), FHA (filamentous hemagglutinin) and pertactin (69K) antigens, said method consisting of vaccinating the subject with a booster vaccine composition comprising a dose of:
   (a) a combination of antigens consisting of 2.5 Lf of the diphtheria (D) toxoid, 5 Lf of the tetanus (T) toxoid, 8 µg of the PT (pertussis toxoid), 8 µg FHA (filamentous hemagglutinin), and 2.5 µg of the pertactin (69K) and
   (b) an adjuvant;
   and wherein said previous vaccination was with a higher dose of each of said antigens present in said DTPa vaccine.

2. The method of claim 1 wherein the adjuvant is aluminum hydroxide.

3. The method of claim 1 wherein the adjuvant is aluminum phosphate.

* * * * *